United States Patent [19]

Hunter et al.

[11] Patent Number: 4,988,500
[45] Date of Patent: Jan. 29, 1991

[54] ORAL COMPOSITIONS

[75] Inventors: Mary A. Hunter, Cincinnati; Joseph W. Pyrz, Hamilton, both of Ohio

[73] Assignee: The Procter & Gamble Company, Cincinnati, Ohio

[21] Appl. No.: 414,986

[22] Filed: Sep. 29, 1989

[51] Int. Cl.$^5$ .................. A61K 7/20; A61K 33/40; A61K 31/78

[52] U.S. Cl. ........................... 424/53; 424/81; 424/613; 424/614; 424/615; 424/616; 514/902; 514/944

[58] Field of Search .............. 424/49, 53, 616, 81, 424/613, 614, 615; 514/944, 902

[56] References Cited

U.S. PATENT DOCUMENTS

| | | | |
|---|---|---|---|
| 2,436,673 | 2/1948 | Shelton | 424/613 |
| 2,542,897 | 2/1951 | Brown et al. | 424/81 |
| 3,011,950 | 12/1961 | Mehaffey | 514/944 |
| 3,485,915 | 12/1969 | Gerstein et al. | 424/81 |
| 3,574,824 | 4/1971 | Echeandia et al. | 424/50 |
| 3,749,773 | 7/1973 | Ninger et al. | 424/81 |
| 3,954,962 | 5/1976 | Prussin | 424/49 |
| 4,132,771 | 1/1979 | Schreiber et al. | 424/49 |
| 4,140,656 | 2/1979 | Mast | 514/944 |
| 4,163,800 | 8/1979 | Wickett et al. | 424/613 |
| 4,187,287 | 2/1980 | Schreiber et al. | 424/49 |
| 4,247,547 | 1/1981 | Marks | 514/944 |
| 4,537,265 | 8/1985 | Gaffar et al. | 454/52 |
| 4,582,701 | 4/1986 | Piechota | 424/52 |
| 4,627,972 | 12/1986 | Gioffre et al. | 424/52 |
| 4,647,451 | 3/1987 | Piechota | 424/52 |
| 4,670,254 | 6/1987 | Kamishita | 424/81 |
| 4,678,666 | 7/1987 | Nozawa et al. | 424/81 |
| 4,687,663 | 8/1987 | Schaeffer | 424/52 |
| 4,692,329 | 9/1987 | Klein et al. | 424/81 |
| 4,775,529 | 10/1988 | Sequeira et al. | 424/81 |
| 4,812,306 | 3/1989 | Cocherell et al. | 424/52 |
| 4,818,518 | 4/1989 | Gioffre et al. | 424/52 |
| 4,826,681 | 5/1989 | Jacquet et al. | 424/613 |
| 4,837,008 | 6/1989 | Rudy et al. | 424/613 |
| 4,867,970 | 9/1989 | Nesham et al. | 424/81 |
| 4,891,211 | 1/1990 | Winston | 424/53 |
| 4,895,721 | 1/1990 | Drucker | 424/53 |

FOREIGN PATENT DOCUMENTS

| | | | |
|---|---|---|---|
| 559142 | 6/1958 | Canada | 424/614 |
| 0271332 | 6/1988 | European Pat. Off. | |
| 56-139415 | 10/1981 | Japan . | |
| 60-146807 | 8/1985 | Japan | 424/616 |
| 1015826A | 1/1986 | Japan . | |
| 61-158907 | 7/1986 | Japan | 424/616 |
| 88/06879 | 9/1988 | PCT Int'l Appl. . | |
| 80059 | 11/1982 | Romania . | |
| 2068225 | 8/1981 | United Kingdom | 424/615 |

*Primary Examiner*—Shep K. Rose
*Attorney, Agent, or Firm*—Douglas C. Mohl; Kim William Zerby; Jack D. Schaeffer

[57] ABSTRACT

Anhydrous oral compositions are disclosed containing an anhydrous humectant and a carboxyvinyl polymer neutralized with an appropriate base.

7 Claims, No Drawings

ORAL COMPOSITIONS

TECHNICAL FIELD

The present invention relates to anhydrous oral compositions containing a nonaqueous humectant and a carboxyvinyl polymer neutralized with an appropriate base.

BACKGROUND ART

There are many materials which have limited solubility in aqueous systems or are unstable in such systems. To overcome these problems, various modifications of the conventional aqueous dentifrice systems have been employed. These range from encapsulating the unstable material to having two separate compositions which are combined just prior to product use.

Another way of improving solubility and stability is to utilize an anhydrous composition. Examples of anhydrous compositions are disclosed in WO 88/06879, Sept. 22, 1988 to Peroxydent Group; and U.S. Pat. No. 4,687,663, Aug. 18, 1987 to Schaeffer.

Although anhydrous systems have been disclosed, there is still the need for improved systems.

The present inventors have surprisingly found that anhydrous dentifrice compositions can be prepared utilizing neutralized carboxyvinyl polymers capable of providing dentifrice viscosities and an anhydrous humectant.

It is an object of the present invention, therefore, to provide such dentifrice compositions.

It is a further object to provide dentifrice compositions utilizing glycerine as the humectant.

It is a further object of the present invention to provide dentifrice compositions utilizing triethanolamine as the neutralizing agent.

These and other objects will become readily apparent from the detailed description which follows. All percentages and ratios herein are by weight and all measurements are made at 25° C. unless otherwise specified.

SUMMARY OF THE INVENTION

The present invention relates to anhydrous dentifrice compositions comprising:
(a) a carboxyvinyl polymer;
(b) a neutralizing agent; and
(c) an anhydrous humectant
wherein the composition has an initial viscosity of from about 12 to about 100 bku's (Brookfield Viscometer, Model D at 50 rpm) and possesses low stickiness and stringiness.

DETAILED DESCRIPTION OF THE INVENTION

The present invention relates to anhydrous dentifrice compositions employing a carboxyvinyl polymer, a neutralizing agent and an anhydrous humectant. These and other components will be described in detail hereinafter.

Carboxyvinyl Polymer

The polymer useful in the present invention can be any carboxyvinyl polymer. Preferred polymers are copolymers of acrylic acid crosslinked with polyallylsucrose as described in U.S. Pat. No. 2,798,053, July 2, 1957 to Brown, incorporated herein by reference. The polymers are provided by B.F. Goodrich Company as, for example, Carbopol 934, 940, 941, and 956. The Carbopol 956 material is preferred.

The carboxyvinyl polymer is used at a level of from about 0.1% to about 1%, preferably from about 0.3% to about 0.8%.

Neutralizinq Agent

The neutralizing agents useful in the present compositions can be any organic alkalizing agents or Lewis bases. The preferred agents are amines such as mono-, di- and triethanol amine and amino acids such as glycine. The most preferred agent is triethanolamine.

The neutralizing agent is used at a level of from about 2% to about 7%, preferably from about 3% to about 5%.

Anhydrous Humectant

Anhydrous humectants useful in the present invention include polyethyleneglycols, propylene glycol and glycerine. Glycerine is the preferred humectant.

The anhydrous humectant is used at a level of from about 5% to about 70%, preferably from about 20% to about 50%.

Optional Components

A preferred optional component useful in the present compositions is a dentifrice abrasive. The abrasive polishing material contemplated for use in the present invention can be any material which does not excessively abrade dentin. These include, for example, silicas including gels and precipitates, calcium carbonate, dicalcium orthophosphate dihydrate, calcium pyrophosphate, tricalcium phosphate, calcium polymetaphosphate, insoluble sodium polymetaphosphate, hydrated alumina, and resinous abrasive materials such as particulate condensation products of urea and formaldehyde, and others such as disclosed by Cooley et al. in U.S. Pat. No. 3,070,510, Dec. 25, 1962, incorporated herein by reference. Mixtures of abrasives may also be used.

Silica dental abrasives, of various types, can provide the unique benefits of exceptional dental cleaning and polishing performance without unduly abrading tooth enamel or dentin. Silica abrasive materials are also exceptionally compatible with sources of soluble fluoride and other ion sources. For these reasons they are preferred for use herein. Of course the abrasive selected should also exhibit excellent compatibility with soluble cationic therapeutic sources.

The silica abrasive polishing materials useful herein, as well as the other abrasives, generally have an average particle size ranging between about 0.1 and 30 microns, preferably 5 and 15 microns. The silica abrasive can be precipitated silica or silica gels such as the silica xerogels described in Pader et al., U.S. Pat. No. 3,538,230, issued Mar. 2, 1970 and DiGiulio, U.S. Pat. No. 3,862,307, June 21, 1975, both incorporated herein by reference. Preferred are the silica xerogels marketed under the tradename "Syloid" by the W. R. Grace & Company, Davison Chemical Division. Preferred precipitated silica materials include those marketed by the J. M. Huber Corporation under the tradename, "Zeodent". These silica abrasive are described in U.S. Pat. No. 4,340,583, July 29, 1982, incorporated herein by reference.

The abrasive in the dentifrice compositions described herein is present at a level of from about 6% to about 70%, preferably from about 15% to about 25% when the dentifrice is a toothpaste.

Flavoring agents can also be added to the dentifrice compositions of the present invention. Suitable flavoring agents include oil of wintergreen, oil of peppermint, oil of spearmint, oil of sassafras, and oil of clove. Sweetening agents are also useful and include aspartame, acesulfame, saccharin, dextrose, levulose and sodium cyclamate. Flavoring and sweetening agents are generally used in the compositions herein at levels of from about 0.005% to about 2% by weight.

The dentifrice compositions of this invention may also contain emulsifying agents. Suitable emulsifying agents are those which are reasonably stable and foam throughout a wide pH range, including non-soap anionic, nonionic, cationic, zwitterionic and amphoteric organic synthetic detergents. Nonionic surfactants are preferred. Many of these suitable surfactants are disclosed by Gieske et al. in U.S. Pat. No. 4,051,234, Sept. 27, 1977 incorporated herein by reference.

Another useful optional component is a soluble fluoride ion source. The number of such sources is great and includes, among others, those disclosed in U.S. Pat. No. 3,535,421, Oct. 20, 1970 to Briner et al. incorporated herein by reference. Typical sources include stannous fluoride, potassium fluoride, indium fluoride, sodium fluoride, sodium monofluorophosphate, alanine hydrofluoride as well as many others. The preferred source is sodium fluoride used at a level sufficient to provide from about 25 ppm $F^-$ to about 2500 ppm.

Another useful agent for incorporation into the present compositions is a soluble pyrophosphate salt such as di and tetra alkali metal pyrophosphate salts as anticalculus agents. These salts are generally used in amounts sufficient to provide at least about 1% $P_2O_7$ species and are described in U.S. Pat. No. 4,515,772, May 7, 1985 to Parran et al. incorporated herein by reference. Also useful are long chain polyphosphates such as ethylenediamine, tetracetic acid; cationic anticalculus agents such as zinc ions; and materials such as phosphocitrate.

Other agents useful in the present compositions are water insoluble vitamins such as Vitamin E acetate and bleaching agents such as sodium perborate and peroxide compounds. These are used at a level of from about 0.1% to about 7%, preferably from about 2% to about 5% for Vitamin E acetate, from about 0.1% to about 20%, preferably from about 5% to about 16% for sodium perborate and 0.1% to about 15%, preferably from about 5% to about 10% for urea peroxide.

Still other agents useful in the present compositions are antibacterial compounds of the type disclosed in European Patent Application 0 251 591, Jan. 7, 1988 to Beecham Group PLC, incorporated herein by reference. A preferred compound is Triclosan, 2, 4, 4'-trichloro-2'-hydroxy phenyl ether, offered by Ciba-Geigy. These materials are used in an amount of about 0.03 to about 1.5, preferably from about 0.1 to about 0.5.

METHOD OF MANUFACTURE A method of manufacturing the compositions of this invention is set forth in the examples.

COMPOSITIONS USE

The compositions of the present invention are generally used in an amount of from about 0.5 g to about 2.0 g, preferably from about 1.0 g to about 1.5 g. The compositions are left in the mouth for a period of from about 10 sec. to about 120 sec., preferably from about 15 sec. to about 60 sec.

The following examples further describe and demonstrate preferred embodiments within the scope of the present invention. The examples are given solely for illustration and are not to be construed as limitations of this invention as many variations thereof are possible without departing from the spirit and scope thereof.

EXAMPLES I-V

The following are compositions exemplary of the present invention.

| Ingredient | I | II | III | IV | V |
|---|---|---|---|---|---|
| Sodium Fluoride | 0.243 | 0.243 | 0.243 | 0.243 | 0.243 |
| Vitamin E Acetate | 5.000 | — | — | — | — |
| Carbamide Peroxide | — | 10.000 | — | — | — |
| Sodium Perborate.4 $H_2O$ | — | — | 16.500 | — | — |
| Sodium Tri-Polyphosphate | — | — | — | 5.000 | — |
| Glycerin | 57.877 | 60.157 | 47.207 | 62.257 | 60.857 |
| Glycine | 6.500 | — | 8.000 | — | 6.500 |
| Triethanoloamine | — | 3.000 | — | 5.000 | — |
| Titanium Dioxide | 0.500 | — | 0.500 | 0.500 | — |
| Saccharin | 0.130 | 0.250 | 0.100 | 0.150 | 0.150 |
| Flavor | 1.000 | 1.000 | 1.200 | 1.000 | 0.900 |
| Sodium Lauryl Sulfate | 1.200 | 0.700 | 1.400 | 1.200 | 1.000 |
| PEG 6 | 3.000 | 2.000 | 4.000 | 2.000 | 6.000 |
| Silica Abrasive | 24.000 | 22.000 | 20.000 | 22.000 | 24.000 |
| Carbopol 956 | 0.500 | 0.600 | 0.800 | 0.600 | 0.300 |
| FD & C Blue #1 | 0.050 | 0.050 | 0.050 | 0.050 | 0.050 |

The above compositions can be made using the following procedure:
1. Glycerine is added to the mix tank and heated to 54° C., which temperature is held throughout the batch.
2. The Vitamin E acetate (or carbamide peroxide, sodium perborate or polyphosphate), glycine, NaF, titanium dioxide and saccharin are added to the tank and thoroughly mixed.
3. The flavor is added to the tank, immediately followed by the alkyl sulfate, this is mixed thoroughly.
4. The PEG 6 is added.
5. The silica is added and the agitator speed is increased as product thickens.
6. The Carbopol is dispersed in a portion of glycerin and added to mix tank and the mixture is mixed thoroughly.
7. The blue due is added.
8. The final batch is mixed for 20 minutes.

What is claimed:
1. An anhydrous oral composition comprising:
    (a) a carboxyvinyl polymer;
    (b) a neutralizing agent;
    (c) a peroxide or perborate compound; and
    (d) an anhydrous humectant; wherein the composition has an initial viscosity of from about 12 to about 100 bku's.
2. A composition according to claim 1 wherein the humectant is selected from the group consisting of polyethylene glycols, propylene glycol and glyercine.
3. A composition according to claim 2 wherein the neutralizing agent is mono-, di-, or triethanolamine.
4. A composition according to claim 3 wherein the active agent is a peroxide compound which is carbamide peroxide.
5. A method of reducing plaque and gingivitis by applying to the oral cavity of a human or lower animal suffering such afflictions a safe and effective amount of a composition according to claim 1.
6. A method according to claim 5 wherein the composition contains glycerine as the humectant.
7. A method according to claim 6 wherein the composition contains a peroxide compound which is caramide peroxide.

* * * * *